Figure 1:
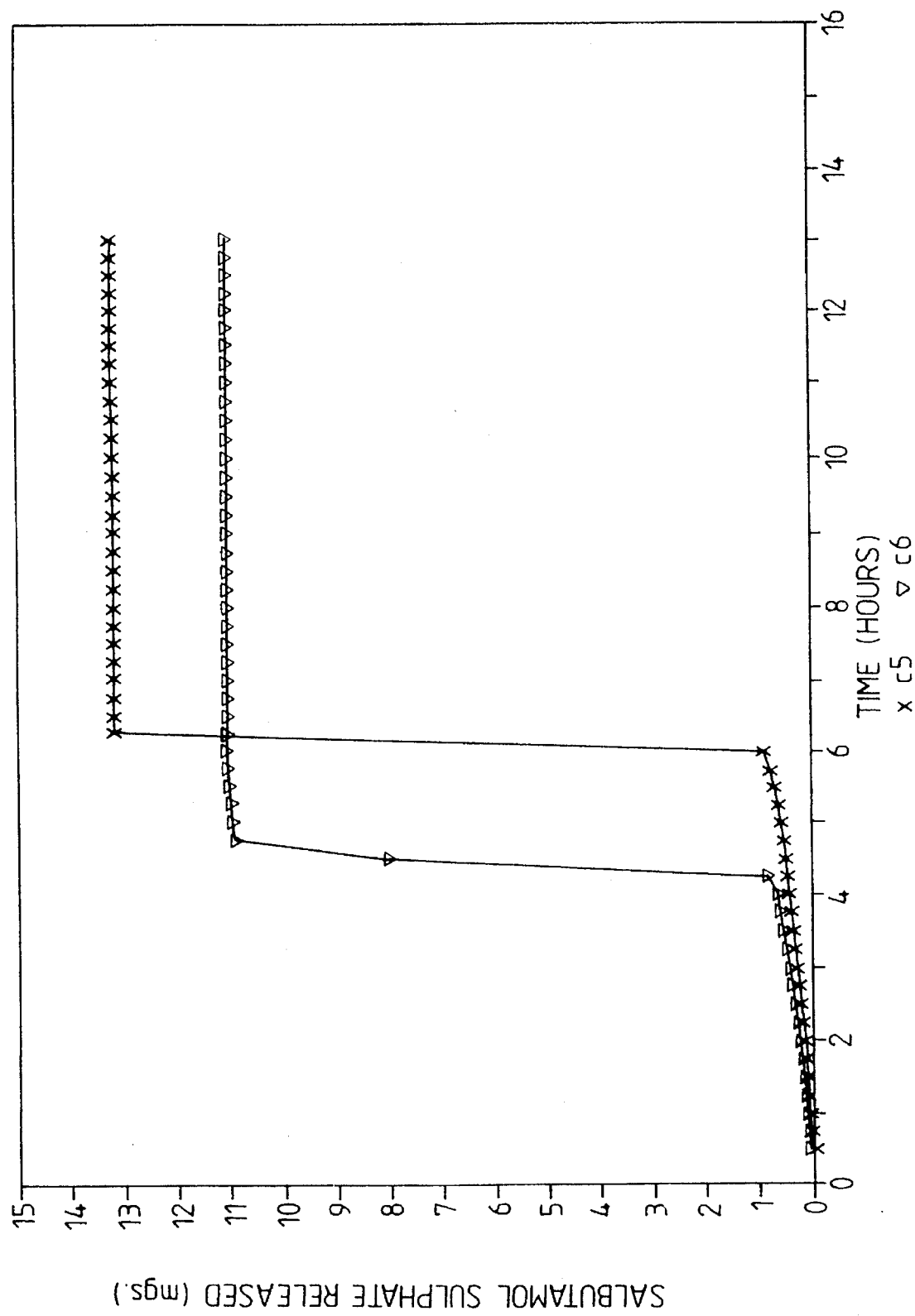

United States Patent [19]

Stevens et al.

[11] Patent Number: 5,474,784
[45] Date of Patent: Dec. 12, 1995

[54] DISPENSING DEVICE

[75] Inventors: Howard N. E. Stevens; Abdul Rashid; Massoud Bakhshaee, all of Glasgow, Scotland

[73] Assignee: British Technology Group Limited, London, England

[21] Appl. No.: 267,744

[22] Filed: Jul. 5, 1994

Related U.S. Application Data

[63] Continuation of Ser. No. 934,478, filed as PCT/GB91/00317, Mar. 1, 1991, abandoned.

[30] Foreign Application Priority Data

Mar. 2, 1990 [GB] United Kingdom ............ 9004702

[51] Int. Cl.[6] .................................. A61K 9/64
[52] U.S. Cl. ..................... 424/456; 424/424; 424/473
[58] Field of Search ........................... 424/456, 471, 424/473, 424

[56] References Cited

U.S. PATENT DOCUMENTS 4,898,733  2/1990  DePizince .................. 424/425
5,082,668  1/1992  Wong ........................ 424/473

FOREIGN PATENT DOCUMENTS

| 0132384 | 5/1985 | European Pat. Off. . |
| 0384646 | 2/1990 | European Pat. Off. . |
| 0384604 | 2/1990 | European Pat. Off. . |
| 2100858 | 6/1972 | France . |
| 436236 | 10/1935 | United Kingdom . |
| 1022171 | 3/1966 | United Kingdom . |
| 1346609 | 2/1974 | United Kingdom . |
| 2057420 | 4/1981 | United Kingdom . |
| 2094256 | 9/1982 | United Kingdom . |
| 2206046 | 6/1988 | United Kingdom . |

Primary Examiner—Thurman K. Page
Assistant Examiner—William E. Benston, Jr.
Attorney, Agent, or Firm—Nixon & Vanderhye

[57] ABSTRACT

A controlled release device useful especially as an oral dosage form for man comprises a water impermeable capsule having at least one orifice which orifice is closed by a water swellable or water dispersable plug. Preferably the capsule is a cylinder formed e.g. of polyethylene closed at one end. The open end is closed by a tablet formed e.g. by direct compression of a pharmaceutical excipient such as lactose.

19 Claims, 7 Drawing Sheets

DISPENSING DEVICE

This is a Rule 62 continuation of application Ser. No. 07/934,478, filed as PCT/GB91/00317, Mar. 2, 1992, now abandoned.

This invention relates to novel devices for the controlled release of an active material into an aqueous environment, particularly the release of a pharmaceutically active drug into the human or the animal body. Specifically this invention relates to hollow devices which are designed to release their contents over a relatively short period following a control led delay after administration.

A wide variety of devices for the controlled release of drugs have been proposed in the art. One of the simplest Is the hard gelatin capsule containing an active material which Is released very shortly after administration as the gelatin is rapidly dissolved. The devices which have been proposed In order to delay that release have been of a complex construction which has severely limited their utilisation.

We have now discovered a novel device which provides a controlled delay after administration after which the contents of the device are released. Such devices comprise a water impermeable capsule having at least one orifice wherein said orifice is closed by the insertion of a plug which is soluble or dispersable in water. Such devices may be constructed simply and economically and enable the pulsed release to be achieved in a controlled and reproducible manner.

Accordingly, from one aspect this invention provides a pulsed release device for releasing the contents of a capsule into an aqueous medium which comprises a water impermeable capsule having at least one orifice wherein the orifice is close with a water soluble or water disperable plug adapted so as to close said orifice.

The water soluble or dispersable plug is preferably designed so as to provide a controlled delay between the introduction of the device into an aqueous environment and the exposure of the contents of the cavity to that environment.

The devices of this invention are preferably constructed so that the area of their exterior surface which is soluble or dispersable comprises only a minor proportion of the total area of the exterior surface of the device. Generally no more than 40% of and preferably less than 20% of the surface area will be formed from water soluble or dispersable materials.

The areas of the water soluble or dispersable material will normally be sufficient to allow the rapid ingress of water into the cavity when the material has dissolved or dispersed, say at least 5% and more preferably at least 10% of the surface area. However, It may constitute a smaller percentage and in some devices such a feature may be preferred. Devices wherein the area of the water soluble material comprises less than 5% and even less than 1% of the total exterior surface area of the device are within the scope of this invention.

The water impermeable portion of the walls may be formed from a variety of materials. They may be of homogeneous construction or they may be laminated. The materials used to form the walls may be impermeable but permeable materials may be utilised provided that the overall construction does not permit the ingress of significant quantities of water prior to the dissolution or dispersion of the soluble portion of the wall. Examples of impermeable materials which may be utilised include polyethylene, polypropylene, poly(methylmethacrylate) polyvinyl chloride, polystyrene, polyurethanes, polytetrafluoroethylene, nylons, polyformaldehydes, cellulose acetate and nitrocellulose.

In the case of oral dosage forms for the administration of pharmaceutically active ingredients the materials used in the construction of the device should be biologically and medically compatible with; non-allergenic and insoluble in and non-irritating to body fluids and tissues. They may be formed from such a material which is biodegradable.

The water soluble or dispersable material is preferably one which can readily be formed into the configuration required for a particular device. Thus materials or blends of materials which are amenable to forming by direct powder compression or by wet granulation and compression or other such techniques are preferred for use in this invention. Those materials known to be useful as excipients in pharmaceutical tablets are generally suitable for use in the formation of the plugs useful in the devices of this invention. Examples of such materials include sugars such as lactose, sucrose, dextrose, sorbitol and mannitol; dextrins; polycarboxylic acids such as ascorbic acid, malic acid, fumaric acid, citric acid and tartaric acid; polyethylene glycols, polyvinyl pyrrolidone, and polyvinylacetate. All of these materials can be compressed to form suitable plugs.

A further group of materials which may be utilised is those which can be processed into a form which disperses or erodes when exposed to an aqueous environment. Examples of materials which may be utilised include inorganic salts such as calcium and magnesium carbonates, calcium phosphate, calcium sulphate, cellulose compounds and derivatives such as microcrystalline cellulose, microfine cellulose and ethyl cellulose, hydrolysed starches, waxes, glycerides and hydrogenated vegetable oils. They may be processed into a dispersable form by the incorporation of a water soluble material (including materials such as those listed above) or by the incorporation of a disintegrant or by a combination of these two approaches. Materials which are useful as disintegrants include all those known in the art of pharmaceutical technology especially starch, carboxymethylstarch, cross-linked PVP and alginic acid and including those sold under the proprietory names Polyplasdone and Acdisol.

The delay in the release of the contents of the cavity varies with the nature of the material used to form the plug and with the manner in which that plug is formed. The actual length of delay provided by a particular plug in a particular device in a controlled environment may be determined by routine experiment. It is within the knowledge of the art to vary the formulation and production of the plugs so as to produce the desired time delay.

These soluble or dispersable materials either separately or a combination may be formed into suitable configurations using classical pharmaceutical techniques. They may further comprise effervescent materials. They may be mixed with pH-sensitive materials such as cellulose acetate phthalate, hydroxypropylmethylcellulose phthalate, polyvinylacetate phthalate and polymethacrylate derivatives. They may comprise an active material which is released into the surrounding environment during the period of dissolution or dispersion prior to the release of the contents of the interior of the capsule.

The devices of this invention may be formed in any convenient shape, for example spheroidal, ellipsoidal or cylindrical. Capsules which are generally cylindrical are preferred. A preferred form of a device according to this invention comprises a hollow cylinder open at one or both ends having a water impermeable construction, said device having a plug of water soluble or dispersable material inserted so as to close the open end or ends. Such devices may be readily formed, e.g. from an extruded plastic tube cut into lengths and optionally sealed at one end.

Alternatively the capsule may be formed by forming a cylinder around a rod; by coating a solution of polymer or organosol onto a former; by compression or injection moulding of a suitable thermoplastic polymer; by powder compression or by direct reaction moulding.

The cylindrical devices are conveniently of a size which may be swallowed and hence they find use as oral dosage forms for man in particular, but also in animals. Typically the length of the hollow cylinder will be in the range 5 to 100 mm, preferably 10 to 30 mm and the external diameter will be in the range 1 mm to 20 mm. Typically the devices will have external dimensions corresponding to those of known oral dosage forms e.g. capsules having sizes in the range triple zero to zero and from 1 to 8. In another embodiment the devices of this invention may be significantly smaller so as to facilitate the inclusion of a plurality of devices in a single dosage form, e.g. a capsule. This enables different release patterns to be obtained.

The orifice in the wall of the capsule may adopt any convenient configuration but in the preferred case will be a circular in cross-section and uniform throughout its depth. Such orifices may readily be closed by the insertion of a right cylindrical plug. The delay in the release of the contents of the capsule is dependant to the depth of any particular plug. The device is constructed so as to ensure that the depth of the walls of the orifice is at least equal to the depth of the plug which is required to be accommodated. In the preferred embodiment the plugs may have a depth of from 0.5 to 10.0 mm more preferably 1.0 to 5.0 mm. The plug will preferably be positioned so that its exposed surface is flush with the exterior wall of the capsule.

The contents of the device may take the form of the active material as such, e.g. as a particulate solid or may take the form of any other convenient dosage form. For example, the active material may be combined with a conventional excipient and be introduced into the device as a powder or as a fluid solution or suspension (provided that the fluid medium does not interact significantly with the materials used to form the walls of the device) or take the form of compressed tablets of excipient and carrier. Either a single tablet or a plurality of such tablets may be introduced. A further alternative is to introduce the active material in a modified dosage form, e.g. a coated material such as is described in British Patent 2112730. This enables the release profile of the device to be modified, e.g. where a crystalline active material is employed it will be released as a single sharp pulse of active material, whereas where a modified dosage form is employed that form will be released into the environment after the pre-determined delay and the subsequent release profile will be that of the modified dosage form. In another preferred embodiment the devices of this invention may provide a multiple pulse release. Such devices comprise a plurality of hollow compartments each separated from the other by a soluble or dispersable wall and arranged so that the contents of the outermost compartment are released before the wall of the next compartment is exposed to the aqueous environment. An example of such a device is a hollow capsule containing alternate layers of active material and plugs formed from soluble or dispersable materials. Any combination of these alternatives may be employed.

The devices of this invention find wide application in medical, including veterinary, contexts and in horticulture and agriculture as well as outside these areas.

Specific classes of drug which may be utilised as the active material in a pulsed release device of this invention include hypnotics, sedatives, tranquilisers, anti-pyretics, anti-inflammatory agents, anti-histamines, anti-tussives, anti-convulsants, anti-asthmatics, muscle relaxants, anti-tumour agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, $\beta$ blockers such as atenolol and metoprolol; calcium antagonists such as nifedipine and nitrendipine, ACE inhibitors such as enalapril and captopril, $\beta_2$ agonists such as salbutamol and terbutaline, preparations containing various substances for the treatment of infection by pathogens including anti-fungal agents, for example metronidazole, anti-parasitic agents and other anti-microbials, anti-malarials, cardiovascular agents, preparations containing hormones, for example androgenic, estrogenic and progestational hormones, notably steroids such as oestradiol, sympathomimetic agents, hypoglycaemic agents, contraceptives, nutritional agents, peptides and proteins, nitrates such as isorbide dinitrate, mononitrate and GTN; xanthines such as theophylline; NSAID's such as piroxicam and diclofenac; benzodiazepines such as triazolam and zopiclone; $\alpha$ blockers such as prazosine and alfuzosine; antivirals such as acyclovir, zidovudine and ampligen, cephalosporins such as cefaclor, antispasmodics such as alverine and salicylates such as 5 amino salicylic acid; preparations containing enzymes of various types of activity, for example chymotrypsin, preparations containing analgesics, for example aspirin, andagents with many other types of action including nematocides and other agents of veterinary application. Mixtures of active substances may be incorporated into the controlled release device.

The controlled release devices of this invention are also useful in the treatment of diabetes and pernicious anaemia where, for example, the controlled release of insulin and cobalamin, respectively, may be utilised.

Moreover, the release devices of this invention are suited to treatment, both prophylactic and therapeutic, of tropical diseases; for example malaria, leprosy, schistosomiasis and clonorchiasis. Examples of drugs which can be used as biologically active substance in release devices of this invention for the treatment of these and other tropical diseases include quinine, sulphonamides, rifamycin, clofazimine, thiambutasine, chlorphenyl derivatives, chlorguamide, cycloguanil, pyrlmethamine, sulphadiazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

The release devices of this invention are also very well suited to veterinary applications. Examples include preparations of antibiotics for general antibacterial activity and also in the treatment of anaplasmosis in cattle; preparations for provision of a wide spectrum of activity against both ectoparasites, for example termites and endoparasites including anthropods, arrested larvae stages of nematodes, lungworms and general strongyles: these may comprise avermectins; preparations for provision of activity against trematode, cestode and roundworm infections: these may comprise amoscanate and praziquantel: preparations for provision of activity against theileria in cattle: these may comprise biologically active naphthoquinones such as menoctone; preparations for provision of activity against babesiosis in cattle, horses and dogs: these may comprise berenil, amidocarb and diampron; preparation for provision of activity against liver fluke in sheep and cattle and against Haemonchus species: these may comprise closantel.

The devices of the present invention may also be combined with another dosage form which will combine the release profile of the novel devices with that of the other dosage form. Thus, for example, two separate devices according to this invention may be joined end to end so that the active materials are separated by a wall or plug. Alternatively a device according to this invention may be joined to any other controlled release device (of appropriate dimensions).

A further preferred embodiment of this invention comprises devices coated with an enteric coating so as to pass through the stomach and release the active material in the intestine. Such devices can be designed so as to release the active a set period after they pass out of the stomach. They may be designed to release in the colon. Any conventional enteric coating agent may be employed for example cellulose acetate phthalate, polyvinyl acetate phthalate, hydroxypropylmethyl cellulose phthalate and polymethacrylate derivatives.

A preferred construction utilises an impermeable coating to cover the exterior of a capsule formed from a water soluble material. The coating may conveniently be formed by dipping a capsule in a solution of any of the above-mentioned materials so as to form a layer which is impermeable to water. The capsule may also be spray coated with solutions of the above materials in which use the exterior has an impermeable coating and the interior may be partially coated. A preferred class of capsules are the conventional hard gelatin capsules coated with a polyvinyl chloride or a polyvinyl chloride acetate copolymer or ethyl cellulose solution. Such devices are advantageous in that they are simple to construct and insofar as their soluble interiors dissolve In the aqueous medium leaving the thin flexible coating to be eliminated from the body.

In use the devices of the invention may be modified so as to resemble known capusles. In particular the cylindrical devices of the preferred embodiments may be combined with a half capsule formed of e.g. hard gelation to form such a device.

The invention is illustrated by the following Examples:

EXAMPLE 1

Two capsules were produced from hollow cylinders of flexible PVC closed at one end. The capsules had a length of 17 mm and an internal diameter of 6.3 mm. A charge of particulate salbutamol sulphate was placed in the Interior of each capsule. The open ends were closed with a tablet formed by compression of Eudragit L100-55 (a proprietary brand of a methacrylic acid—ethyl acrylate copolymer and sold by the Rohm-Pharma company). In the first instance 56 mg of Eudragit was compressed in a die of diameter 7.18 mm to form a tablet having a thickness of 1.27 mm. In the second instance 47 mg of Eudragit was compressed in the same die to form a tablet having a thickness of 1.07 mm.

The release profile of these devices in water was measured using a US Pharmacopeia dissolution bath in which the aqueous medium was a buffer solution having a pH of 7.6 The results are shown in FIG. 1 in which the results for the first device are indicated as X and for the second as ∇.

EXAMPLE 2

Two multiple pulse release devices were prepared using a capsule formed from flexible PVC identical to that used in Example 1 which was filled with alternate layers of salbutamol sulphate and compressed tablets made from Eudragit L100-55 using the quantities shown In the following table (listing the compositions in ascending order starting with the layer placed at the bottom, the closed end, of the capsule).

TABLE 1

|  | Device 1 | Device 2 |
| --- | --- | --- |
| Salbutamol | 10.1 mg | 9.5 mg |
| Eudragit | 48.8 mg | 49.3 mg |
| Salbutamol | 9.7 mg | 9.9 mg |
| Eudragit | 49.7 mg | 50.3 mg |
| Salbutamol | 9.3 mg | 10.2 mg |
| Eudragit | 49.1 mg | 50.0 mg |
| Salbutamol | 9.4 mg | 9.8 mg |
| Eudragit | 48.5 mg | 51.1 mg |

Figure 2:
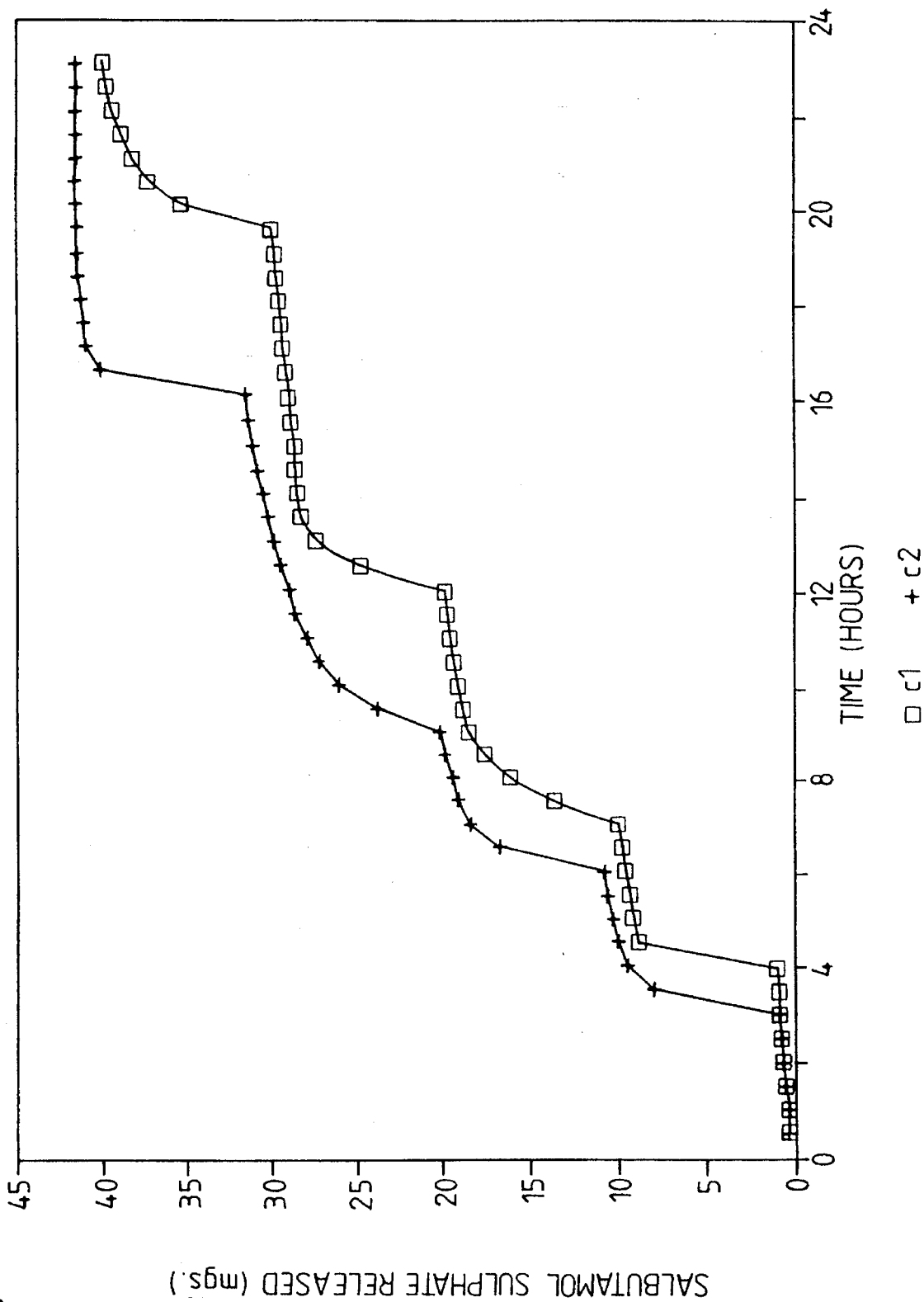

The release profile was tested using the same procedure as In Example 1. The results are shown in FIG. 2 (the first device indicated as □ and the second as +).

EXAMPLE 3

Three pulsed release devices were assembled using a capsule made from low density polyethylene (LDPE) having an overall length of 18 mm, an internal diameter of 6.33 mm and a wall thickness of 20 thousandth of an inch which were filled with sodium chloride and salbutamol sulphate placed such that the drug was positioned just below the soluble plug. The soluble plug was prepared by compacting a mixture of lactose (98.5 wt %), Aerosil 200 (1 wt %) and Magnesium Stearate (0.5 wt %) on Manesty Type F3 Tabletting Machine. Details are shown in Table 2 below.

TABLE 2

|  | Device Number | | |
| --- | --- | --- | --- |
|  | 4 | 5 | 6 |
| Salbutamol (mg) | 9.2 | 9.1 | 10.1 |
| Sodium Chloride (mg) | 504.8 | 516.3 | 514.9 |
| Soluble Plug |  |  |  |
| Diameter (mm) | 6.4 | 6.4 | 6.4 |
| Thickness (mm) | 2.81 | 2.81 | 2.81 |
| Weight (mg) | 120 | 120 | 120 |

Figure 3:
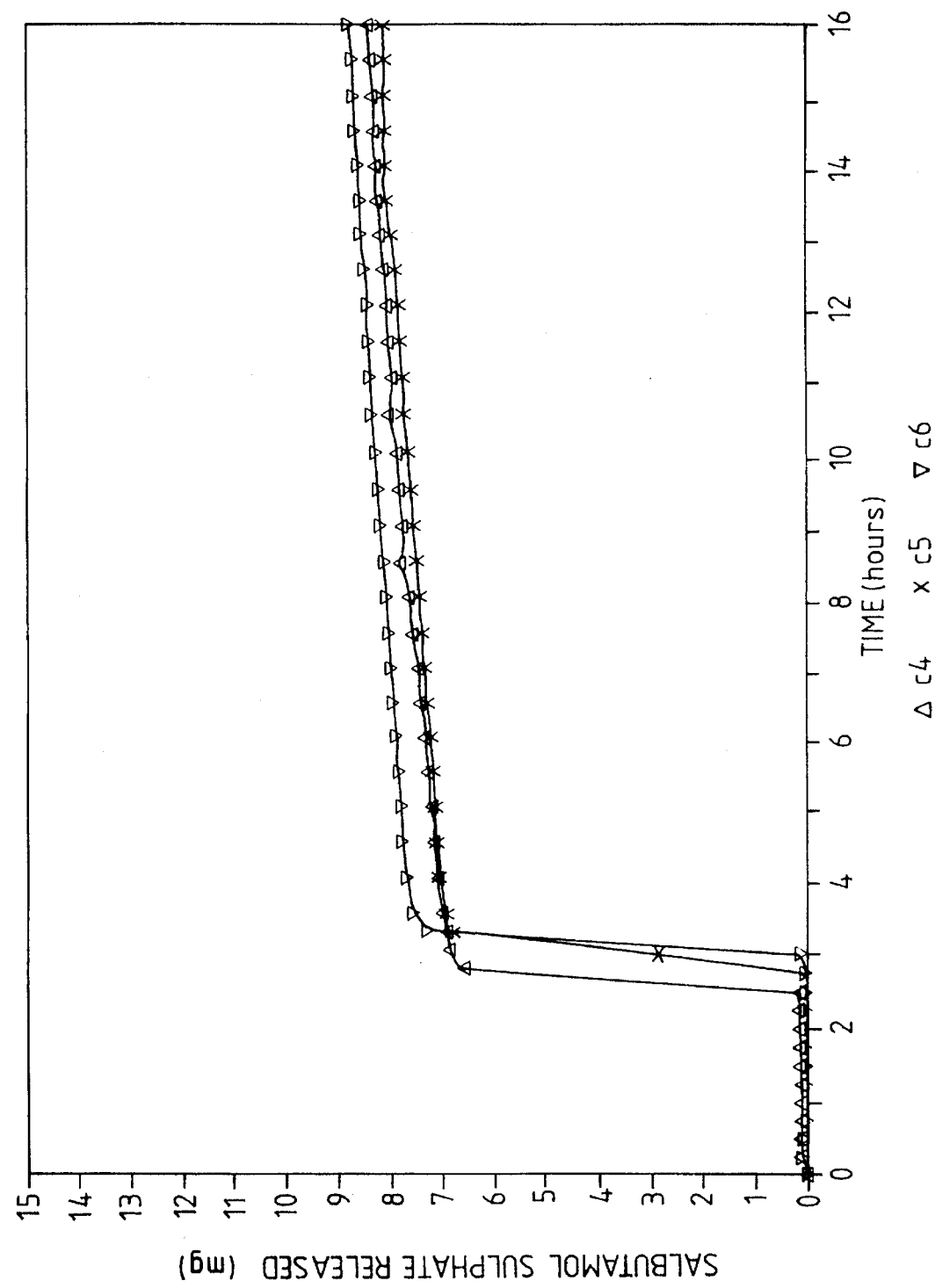

The release profile was determined in water using the same procedure as described in Example 1. The results are graphically shown in FIG. 3.

EXAMPLE 4

Figure 4:
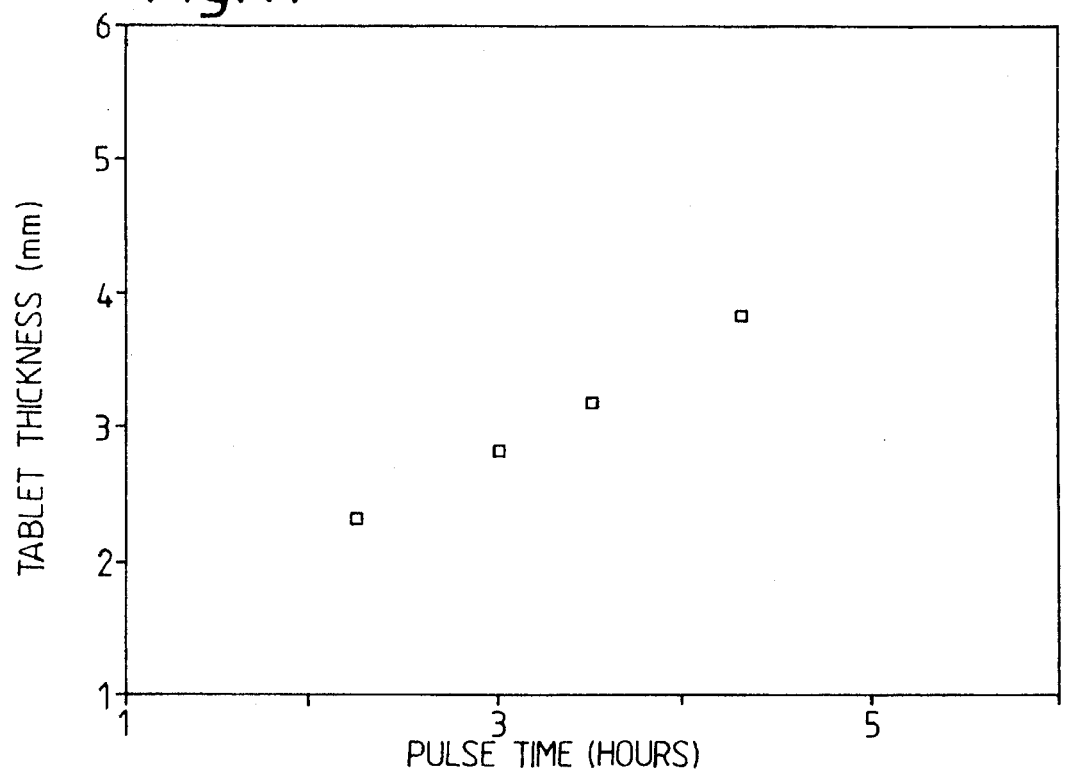
Figure 5:
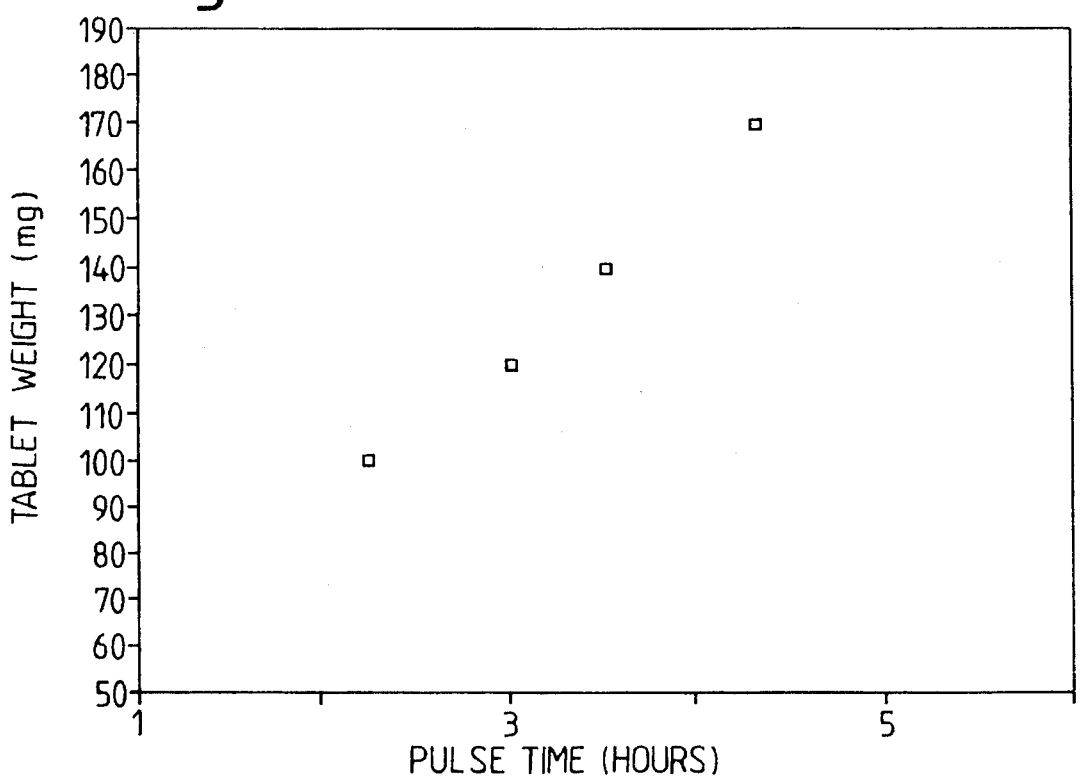

Several devices were assembled by utilising the same components (i.e. same capsule, same plug formulation) as in Example 3 but the thickness and weight of the plug was varied. The devices were tested as per Example 3 and the mean results are shown in FIGS. 4, 5 and in Table 3 below.

TABLE 3

| MEAN TABLET WT (mg) | MEAN THICKNESS (Mm) | MEAN PULSE TIME (h) |
| --- | --- | --- |
| 100 | 2.3 | 2.25 |
| 120 | 2.81 | 3.00 |
| 140 | 3.16 | 3.50 |
| 170 | 3.82 | 4.30 |

EXAMPLE 5

Four devices were prepared by utilising the capsule identical to that used in Example 4. The soluble plugs were prepared by compacting a mixture of lactose (70 wt %), Polyvinyl pyrrolidone (m wt 700,000) (20 wt %) and Magnesium Stearate (1 wt %) on Manesty F3 type tabletting machine. The details are shown in Table 4 below.

TABLE 4

|  | Device Number | | | |
| --- | --- | --- | --- | --- |
|  | 1 | 2 | 3 | 4 |
| Sodium Chloride (mg) | 505.2 | 504.7 | 515.0 | 513.0 |
| Salbutamol sulphate (mg) | 10.4 | 10.2 | 9.7 | 10.5 |
| Soluble Plug |  |  |  |  |
| Diameter (mm) | 6.4 | 6.4 | 6.4 | 6.4 |
| Thickness (mm) | 3.06 | 3.10 | 4.26 | 4.23 |
| Weight (mg) | 118.7 | 120.5 | 169.1 | 167.6 |

Figure 6:
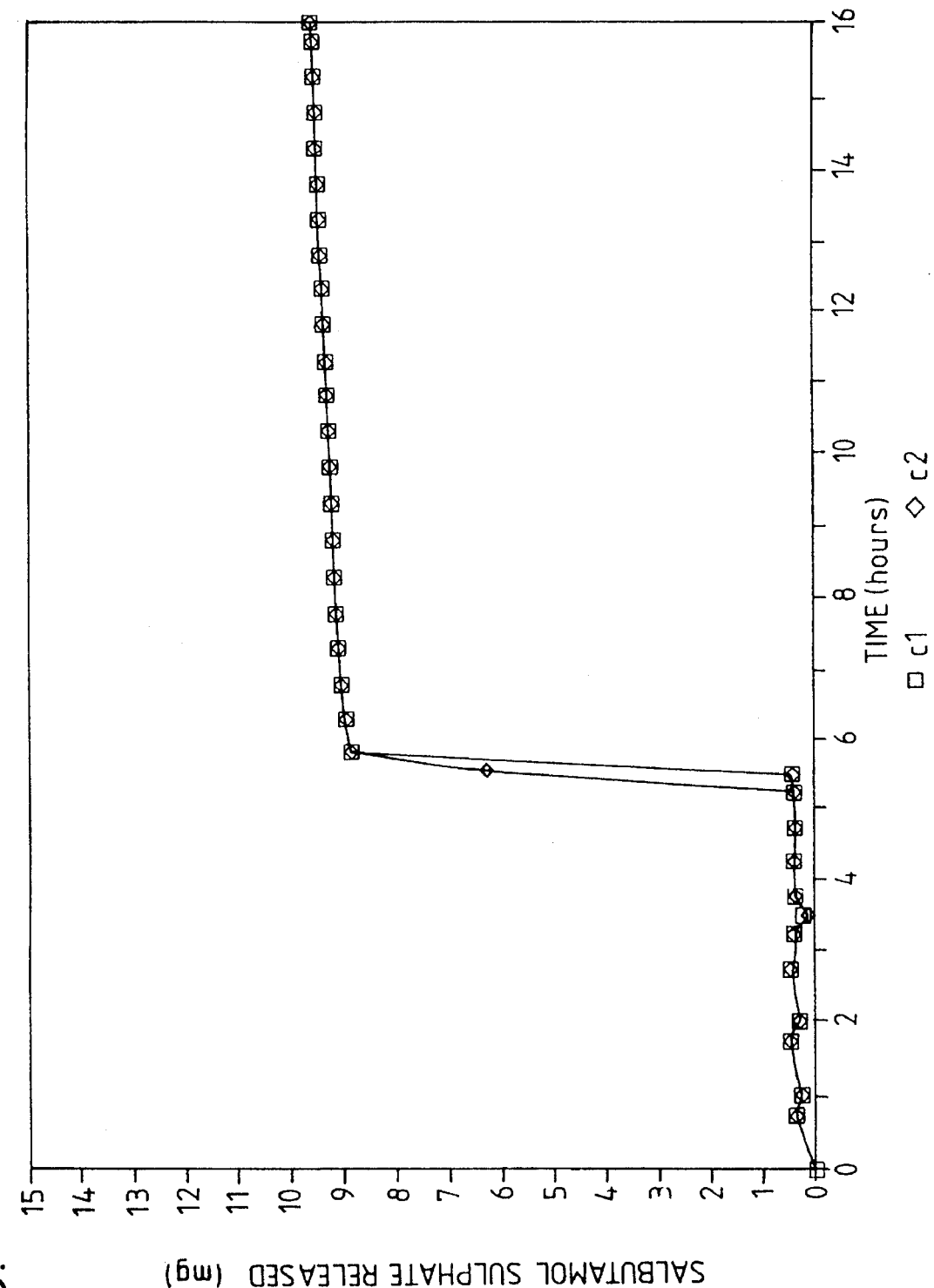
Figure 7:
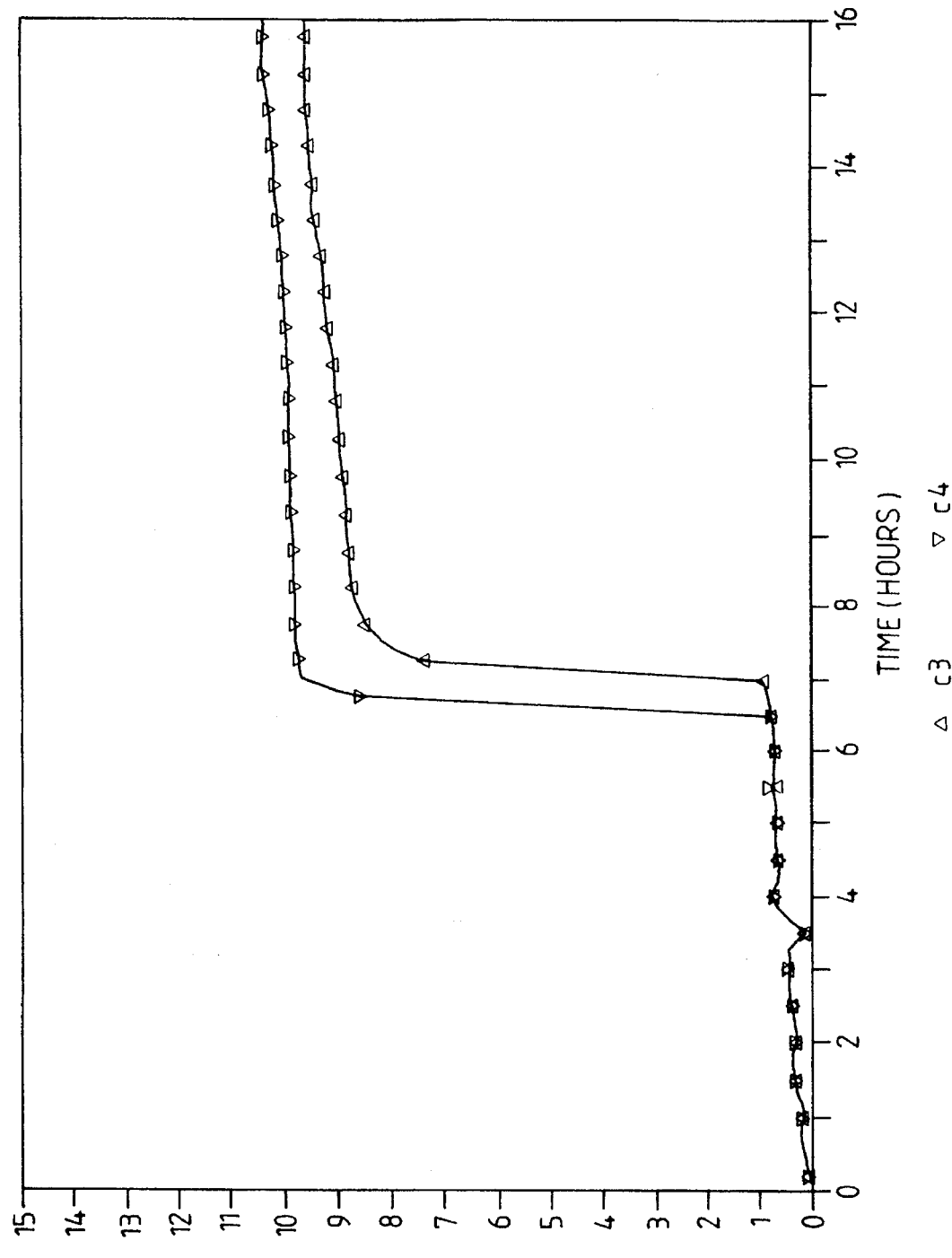

The release profiles were determined using the same procedure as described in Example 3. The results are shown in FIGS. 6 and 7.

EXAMPLE 6

Six devices were prepared by utilising the capsule described in Example 5. The plug was prepared by compacting a mixture of lactose (79 wt %), Polyethylene glycol Mn 8000 (20 wt %) and Magnesium Stearate (1 wt %) on a Manesty F3 tabletting machine. Details are shown in Table 5 below.

TABLE 5

|  | Device Number | | | | | |
| --- | --- | --- | --- | --- | --- | --- |
|  | 1 □ | 2 + | 3 ◊ | 4 Δ | 5 X | 6 ▽ |
| Sodium Chloride (mg) | 610.4 | 609.7 | 609.4 | 545.6 | 545.6 | 545.5 |
| Salbutamol | 9.6 | 9.4 | 9.9 | 9.5 | 10.3 | 10.2 |
| sulphate (mg) |  |  |  |  |  |  |
| Soluble Plug |  |  |  |  |  |  |
| Diameter (mm) | 6.4 | 6.4 | 6.4 | 6.4 | 6.4 | 6.4 |
| Thickness (mm) | 2.2 | 2.2 | 2.2 | 3.8 | 3.8 | 3.8 |
| Weight (mg) | 98.0 | 98.0 | 98.0 | 166.5 | 166.5 | 166.5 |

Figure 8:
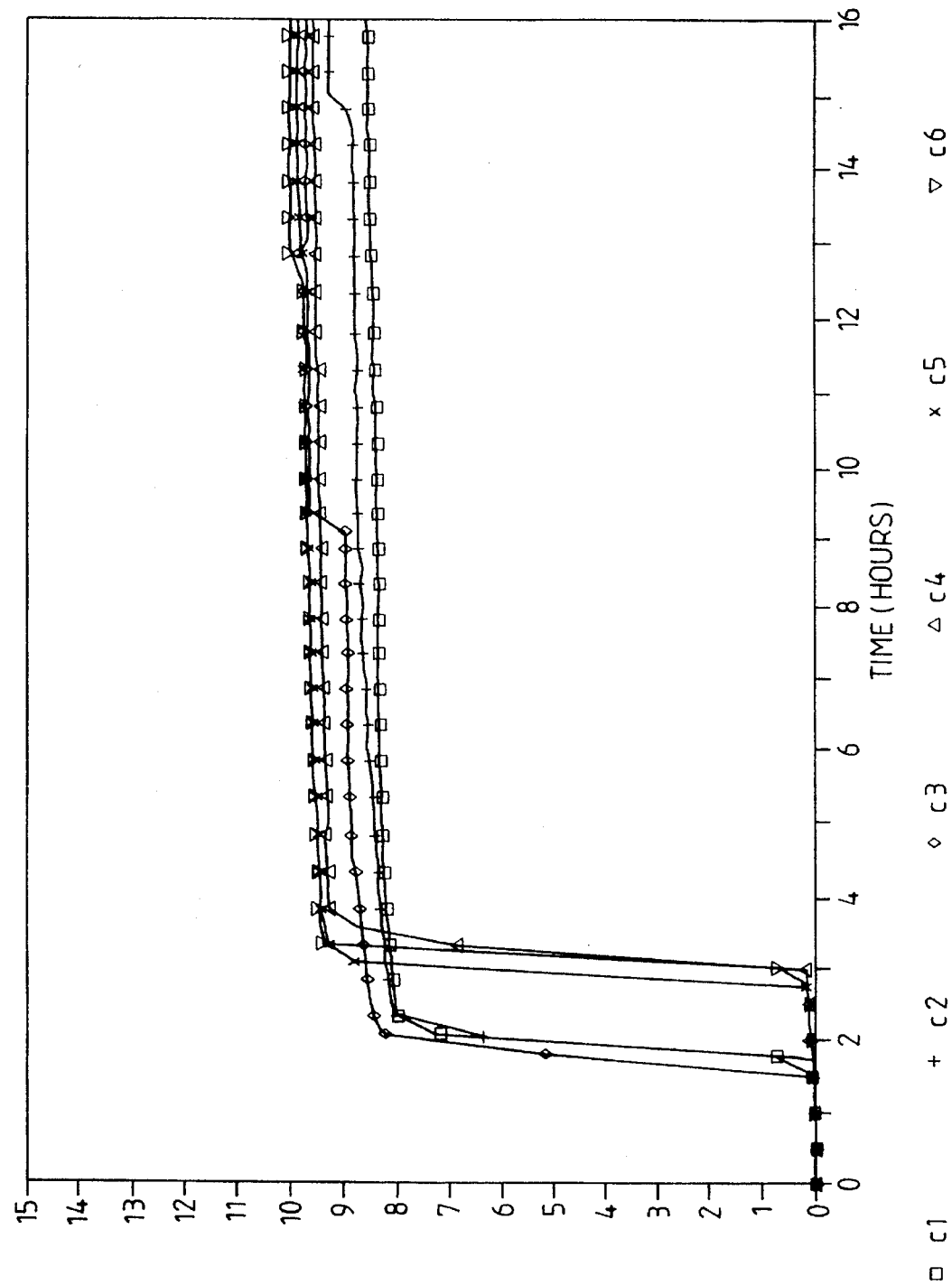

The release profile was determined as in Example 3. The results are shown graphically in FIG. 8.

EXAMPLE 7

A series of devices were prepared utilising the capsule described in Example 3. A series of tablets were prepared using the following excepients.

Lactose (LAC)
Aerosil 2000 (AER)
PVP (Polyvinylpyrolidene M.W. 700,000)—(PVP)
CUTINA HR (CUT) *
Magnesium steurate (Mg St)

* a hydrogenated vegetable oil sold by the Henkel Company.

The appropriate quantities of the excipients were weighed in a glass jar. The jar was secured with a lid and the contents mixed using a Turbula mixer for the time specified in the Table. The mixture was then compressed into tablets of various weights using a Manesty F3 tabletting machine. The open end of the capsule was closed by placing the tablet in the flush position and the dissolution time determined in the manner described in Example 1. The results are shown in the following table.

TABLE 1

| Tablet Formation | Ratio of Components (wt %) | Mixing Time (min) | Average Tablet Weight (mg) | Average Tablet Thickness (mm) | Average Pulse Time (hr) |
| --- | --- | --- | --- | --- | --- |
| LAC/AER/MG St | 98.5/1/0.5 | 15 | 140 | 3.16 | 3.43 |
| " | " | 15 | 170 | 3.82 | 4.30 |
| LAC/PVP/MG St | 79/20/1 | 15 | 150.1 | 3.49 | 4.40 |
| LAC/CUT/Mg St | 96/3/1 | 15 | 119.0 | 2.66 | 5.45 |
| " | 98/1/1 | 20 | 145.3 | 3.21 | 7.52 |
| LAC/Mg St | 98/2 | 15 | 170.4 | 3.74 | 9.04 |
| " | " | 15 | 120.2 | 2.62 | 5.00 |
| " | 98.25/1.75 | 30 | 169.7 | 3.75 | 8.34 |
| " | " | 60 | 171.2 | 3.78 | 9.14 |
| " | 98/2 | 60 | 169.5 | 3.80 | 9.56 |
| " | " | 60 | 145.2 | 3.20 | 7.88 |
| " | " | 60 | 120.3 | 2.65 | 5.96 |
| LAC/Mg St (MULTIPULSE) | 98.5/1.5 | 60 | 121.5 | 2.65 | 4.46 |
|  |  |  | 120.5 | 2.63 | 11.58 |
|  |  |  | 120.7 | 2.63 | 21.71 |
|  |  |  | 120.8 | 2.63 | 31.92 |

EXAMPLE 8

A series of devices were made up in the manner described in Example 7 using the following excipients:

CUTINA (CUT)
EMCOSOY (EMCO)*
EXPLOTAB (EXPLO)+

* a soya polysaccharide excipient sold by Forum Chemicals Ltd.
+ a sodium starch glycollate disintegrant sold by Forum Chemicals Ltd.

The compositions of the tablets are the results obtained are summarised in Table 2.

TABLE 2

| Tablet Formation | Ratio of Components (wt %) | Mixing Time (min) | Average Tablet Weight (mg) | Average Tablet Thickness (mm) | Average Pulse Time (hr) |
| --- | --- | --- | --- | --- | --- |
| CUT/EMCO.LAC | 70:15:15 | 25 | 114.3 | 3.65 | 6.42 |
| CUT/EXPLO | 80:20 | 25 | 125.2 | 3.69 | 7.33 |
| Mg St added as 0.5% of total weight in both cases | | | | | |

We claim:

1. A capsule suitable for human oral administration, comprising:
   (a) a hollow body having a water-impermeable external surface and an orifice through which the contents of the hollow body are to be released as a pulse in the human body; and
   (b) a plug consisting essentially of a water-soluble or water-dispersible material closing said orifice, wherein said plug provides a pulsed release of the capsule contents after a controlled delay between introduction of the capsule into an aqueous environment and exposure of the capsule contents to said environment, said plug being composed of a compressed pharmaceutically acceptable material.

2. A capsule according to claim 1, in the form of a hollow cylinder having an orifice at one or both ends.

3. A capsule according to claim 1, having a length of from 10 to 30 mm.

4. A capsule according to claim 1, in which the exposed area of the plug comprises no more than 40% of the total exterior surface area of the capsule.

5. A capsule according to claim 1, in which the exposed surface of the plug is flush with the end of the capsule.

6. A capsule according to claim 1, in which the plug has a depth of from 0.5 to 10.0 mm.

7. A capsule according to claim 6, in which the plug has a depth of from 1.0 to 5.0 mm.

8. A capsule according to claim 1, in which the plug is formed from a sugar.

9. A capsule according to claim 1, in which the plug is formed from a cellulose compound or derivative.

10. A capsule according to claim 1, formed from a water impermeable material selected from the group consisting of polyethylene, polypropylene, poly (methylmethacrylate), polyvinyl chloride, polystyrene, polyurethanes, polytetrafluoroethylene, nylons, polyformaldehydes, polyesters, cellulose acetate and nitro cellulose.

11. A capsule according to claim 10, in which the water impermeable material is a thermoplastic.

12. A capsule according to claim 10, in which the water impermeable material is a low density polyethylene.

13. A capsule according to claim 11, in which the capsule is formed from a water soluble material coated with a water impermeable material.

14. A capsule according to claim 13, in which the water soluble material is gelatin or starch.

15. A capsule according to claim 13, in which the impermeable coating is polyvinyl chloride.

16. A capsule according to claim 1, containing a pharmaceutically active compound.

17. A capsule according to claim 16, in which the active material is a particulate solid.

18. A capsule according to claim 17, in which the active compound is present as a modified dosage form.

19. A capsule according to claim 1, having an external surface provided with an enteric coating.

* * * * *